US008278941B2

(12) United States Patent
Kroh et al.

(10) Patent No.: US 8,278,941 B2
(45) Date of Patent: Oct. 2, 2012

(54) STRAIN MONITORING SYSTEM AND APPARATUS

(75) Inventors: Jason Kroh, Villa Rica, GA (US);
Florent Cros, Decatur, GA (US);
Christophe Courcimault, Avondale Estates, GA (US)

(73) Assignee: CardioMems, Inc., Atlanta, GA (US)

( * ) Notice: Subject to any disclaimer, the term of this patent is extended or adjusted under 35 U.S.C. 154(b) by 694 days.

(21) Appl. No.: 12/416,916

(22) Filed: Apr. 1, 2009

(65) Prior Publication Data

US 2009/0273353 A1  Nov. 5, 2009

Related U.S. Application Data

(60) Continuation-in-part of application No. 11/613,645, filed on Dec. 20, 2006, now Pat. No. 7,550,978, which is a continuation of application No. 11/105,294, filed on Apr. 13, 2005, now Pat. No. 7,245,117, application No. 12/416,916, which is a continuation-in-part of application No. 11/717,967, filed on Mar. 14, 2007, now Pat. No. 7,466,120, which is a continuation-in-part of application No. 11/276,571, filed on Mar. 6, 2006, now Pat. No. 7,498,799, which is a continuation-in-part of application No. 11/105,294, filed on Apr. 13, 2005, now Pat. No. 7,245,117, application No. 12/416,916, which is a continuation-in-part of application No. 12/175,803, filed on Jul. 18, 2008, which is a division of application No. 11/472,905, filed on Jun. 22, 2006, which is a division of application No. 10/943,772, filed on Sep. 16, 2004, now abandoned, application No. 12/416,916, which is a continuation-in-part of application No. 11/157,375, filed on Jun. 21, 2005.

(60) Provisional application No. 60/623,959, filed on Nov. 1, 2004, provisional application No. 60/782,313, filed on Mar. 14, 2006, provisional application No. 60/503,745, filed on Sep. 16, 2003, provisional application No. 61/072,715, filed on Apr. 1, 2008.

(51) Int. Cl.
*G01R 27/02* (2006.01)

(52) U.S. Cl. ........................................... 324/633

(58) Field of Classification Search .................. None
See application file for complete search history.

(56) References Cited

U.S. PATENT DOCUMENTS 4,651,571 A * 3/1987 McGlade ........................ 73/773

(Continued)

FOREIGN PATENT DOCUMENTS

WO  WO 2009146090 A1 * 12/2009

OTHER PUBLICATIONS

International Search Report and the Written Opinion for International Application No. PCT/US2009/039222 (mailed Nov. 12, 2009).

*Primary Examiner* — Paresh Patel
(74) *Attorney, Agent, or Firm* — Ballard Spahr LLP

(57) ABSTRACT

This application relates to an apparatus and system for sensing strain on a portion of an implant positioned in a living being. In one aspect, the apparatus has at least one sensor assembly that can be mountable thereon a portion of the implant and that has a passive electrical resonant circuit that can be configured to be selectively electromagnetically coupled to an ex-vivo source of RF energy. Each sensor assembly, in response to the electromagnetic coupling, can be configured to generate an output signal characterized by a frequency that is dependent upon urged movement of a portion of the passive electrical resonant circuit and is indicative of strain applied thereon a portion of the respective sensor assembly.

44 Claims, 13 Drawing Sheets

U.S. PATENT DOCUMENTS

| | | |
|---|---|---|
| 6,667,725 B1 | 12/2003 | Simons et al. |
| 6,743,173 B2 | 6/2004 | Penner et al. |
| 7,432,723 B2 * | 10/2008 | Ellis et al. .................... 324/654 |
| 7,621,878 B2 * | 11/2009 | Ericson et al. ................ 600/561 |
| 2004/0113790 A1 | 6/2004 | Hamel et al. |
| 2004/0118997 A1 * | 6/2004 | Lehmann et al. ........ 250/227.14 |
| 2006/0052782 A1 | 3/2006 | Morgan et al. |

* cited by examiner

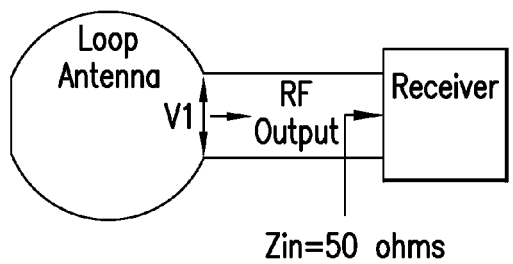
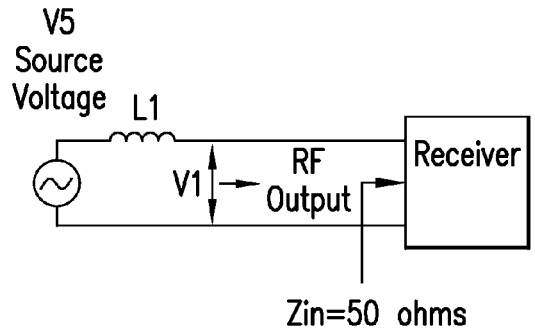
FIG.12A  FIG.12B
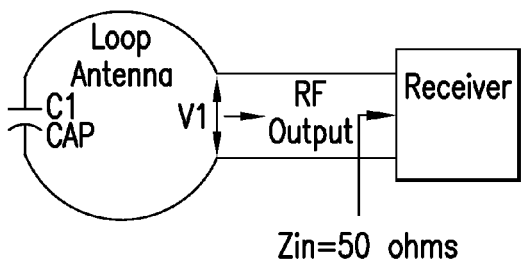
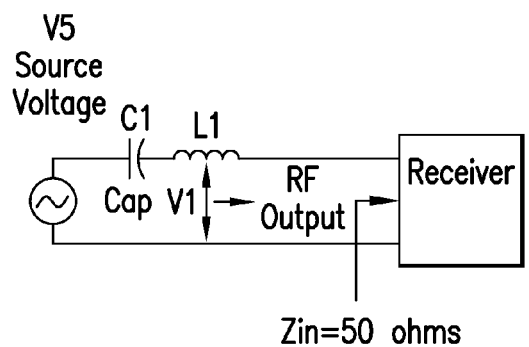
FIG.13A  FIG.13B
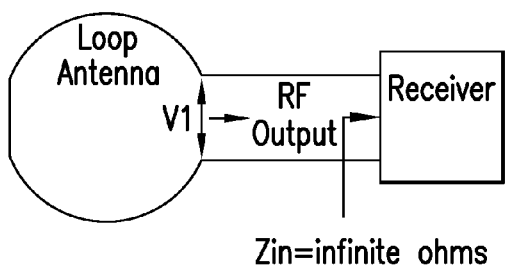
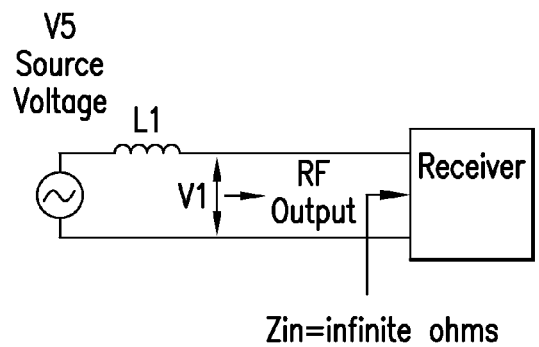
FIG.14A  FIG.14B

STRAIN MONITORING SYSTEM AND APPARATUS

This application is a continuation-in-part of U.S. patent application Ser. No. 11/613,645, filed on Dec. 20, 2006 now U.S. Pat. No. 7,550,978, which is a continuation of U.S. patent application Ser. No. 11/105,294, filed on Apr. 13, 2005, now U.S. Pat. No. 7,245,117, which claims priority to U.S. Provisional Application No. 60/623,959, filed on Nov. 1, 2004. This application is also a continuation-in-part of U.S. patent application Ser. No. 11/717,967, filed on Mar. 14, 2007, now U.S. Pat. No. 7,466,120, which is a continuation-in-part of U.S. patent application Ser. No. 11/276,571, filed on Mar. 6, 2006, now U.S. Pat. No. 7,498,799 which is a continuation-in-part of U.S. patent application Ser. No. 11/105,294, filed on Apr. 13, 2005, now U.S. Pat. No. 7,245,117, which claims priority to U.S. Provisional Application No. 60/623,959, filed on Nov. 1, 2004. U.S. patent application Ser. No. 11/717,967 also claims priority to U.S. Provisional Application No. 60/782,313, filed on Mar. 14, 2006. Further, this application is a continuation-in-part of pending U.S. patent application Ser. No. 12/175,803, filed on Jul. 18, 2008, which is a divisional of pending U.S. patent application Ser. No. 11/472,905, filed on Jun. 22, 2006, which is a divisional of abandoned U.S. patent application Ser. No. 10/943,772, filed on Sep. 16, 2004, which claims priority to U.S. Provisional Application No. 60/503,745, filed on Sep. 16, 2003. Additionally, this application is a continuation-in-part of pending U.S. patent application Ser. No. 11/157,375, filed on Jun. 21, 2005. This application also claims priority to U.S. Provisional Application No. 61/072,715, filed on Apr. 1, 2008.

BACKGROUND OF THE INVENTION

1. Field of the Invention

This invention pertains generally to monitoring strain thereon portions of implants positioned within a living being, and more particularly to using strain monitoring as an indicator of medical conditions including, without limitation, monitoring the progress of spinal fusion and measuring spinal loading.

2. Background Art

Lumbar fusion is one of the fastest growing areas of orthopedic surgery. A lumbar fusion is commonly recommended for diagnoses such as, for example, a recurrent disc herniation, lumbar spondylolisthesis, scoliosis or curvature of the spine, severe disc degeneration, or for a traumatic injury of the spine such as a fracture. All of these different conditions can cause back and leg pain, which can result in debilitation and prevents the patient from enjoying ordinary daily activities. Of course, other circumstances or conditions exist in which a fusion is the best treatment for the particular source of back and leg pain.

Lumbar fusion procedures promote the permanent fusion of two or more vertebral bones together to maintain alignment and provide stability and strength. The fusion created linking bridge of solid bone effectively eliminates motion across the damaged level, which results in a reduction of pain experienced by the patient. Lumbar fusion methodologies are conventional and include different approaches to the spine, such as, for example and without limitation, anterior and posterior approaches.

Conventional lumbar fusion methodologies typically use a spinal artificial support that is deployed during surgery. The spinal artificial support is fixed to targeted body tissues and serves as an initial support to help fixate the respective vertebrae of interest until bone growth, which can be stimulated by a bone growth factor, operably fills the area between the respective vertebrae of interest to eliminates motion between the vertebrae. The spinal artificial support can become at least partially encapsulated during the bone growth process.

In one example, a pedicle screw is screwed from the posterior through the pedicle bony bridge of the vertebrae and into the wall the vertebral body. This procedure is repeated for the neighboring vertebrae and bilaterally on the opposite side of the posterior spine. Once all four pedicle screws are in place, a rod or plate is mounted thereon at least two of the pedicle screws. The rod or plate is then held down with locking nuts that screw onto the posts. In another example, an intravertebrael cage can be mounted therein the disk space. In either example, after the spinal artificial support is fixated into the desired position, it is conventional to add bone graft material in and about the intravertebrael space to encourage the growth of bone between the adjacent vertebrae of interest.

The process of healing a fusion can take many months or well over a year to be complete. Conventionally, after surgery, the patient is immobilized with a brace that extends from beneath the arms to midline of the hips and is instructed not to perform any strenuous physical activity for an extended period of time which results is atrophy of the muscles of the spine and abdomen from disuse.

One difficulty is that the biomechanical properties of a stable spinal fusion typically precedes the radiographic appearance of a solid fusion by at least eight weeks, which makes it difficult for a physician to monitor the efficacy of the fusion protocol. However, as the bone-fusion process matures the load-sharing of the spinal artificial support changes. It has been found that the load-sharing of the spinal artificial support, and particularly the bending stress thereon the spinal artificial support decreases concurrently with the development of the spinal fusion.

Presently, the onset of spinal fusion after lumbar surgery continues to be difficult to determine, and, even though the implant provides internal fixation in a much shorter period of time, patients are frequently required to wear the brace for extended periods of time with the resulting detrimental effects to the patient's musculature. There is a need for an approach that allows the physician to monitor the fusion process to maximize the outcome of the spinal fusion process.

SUMMARY

This application relates to an apparatus and system for sensing strain on a portion of an implant positioned in a living being. In one aspect, the apparatus comprises at least one sensor assembly that can be mountable thereon a portion of the implant. In another aspect, the at least on sensor assembly can comprise a passive electrical resonant circuit that is configured to be selectively electromagnetically coupled to an ex-vivo source of RF energy. In this aspect, each sensor assembly, in response to the electromagnetic coupling, can be configured to generate an output signal characterized by a frequency that is dependent upon urged movement of a portion of the passive electrical resonant circuit and is indicative of strain applied thereon a portion of the respective sensor assembly. In one aspect, it is contemplated that the passive electrical resonant circuit of the at least one sensor assembly comprises a LC resonant circuit.

In operation, the at least one sensor assembly can be operably coupled to an exterior surface of the implant, and upon application a moment force thereon the implant, at least a portion of the passive electrical resonant circuit of the at least one sensor assembly can be forced or otherwise urged to move with a resultant change in the resonant frequency of the at least one sensor assembly when it is energized via the electromagnetic coupling. The sensed frequency of the "strained" at least one sensor assembly is indicative of the strain being imposed thereon the implant.

DETAILED DESCRIPTION OF THE FIGURES

These and other features of the preferred embodiments of the invention will become more apparent in the detailed description in which reference is made to the appended drawings wherein.

Figure 7:
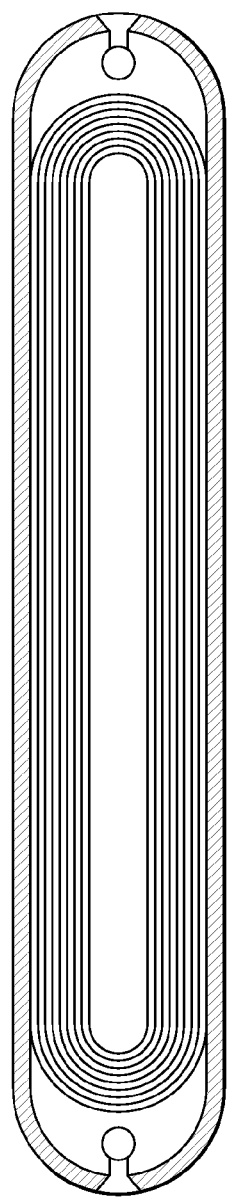

FIG. 7 schematically illustrates an exemplary substantially planar LC resonant circuit.

Figure 8:
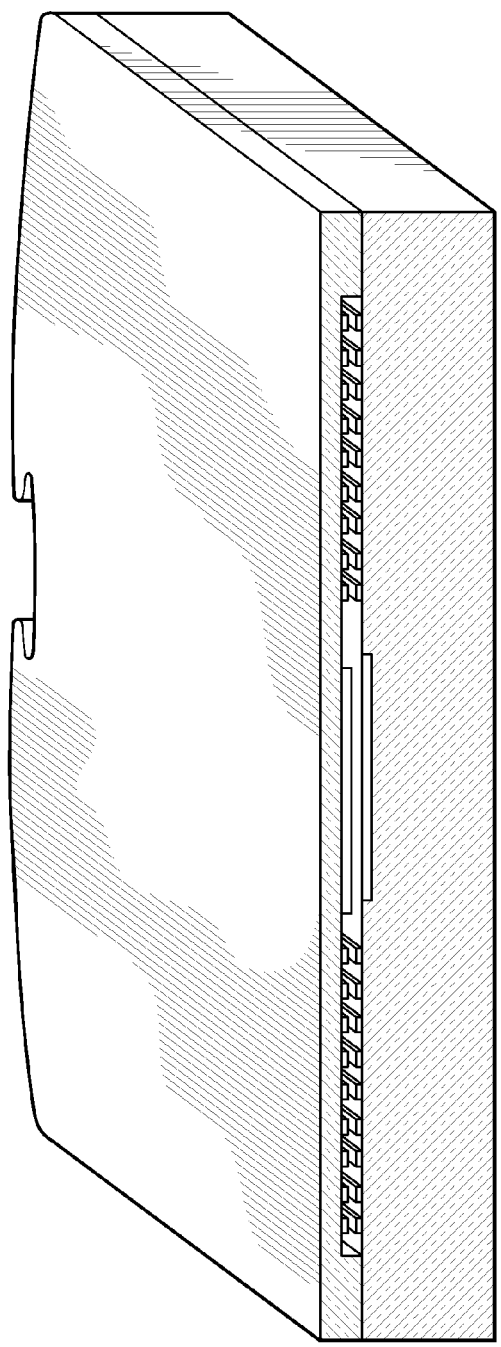

FIG. 8 is an exemplary cross-sectional perspective view of the LC resonant circuit of FIG. 7.

Figure 9:
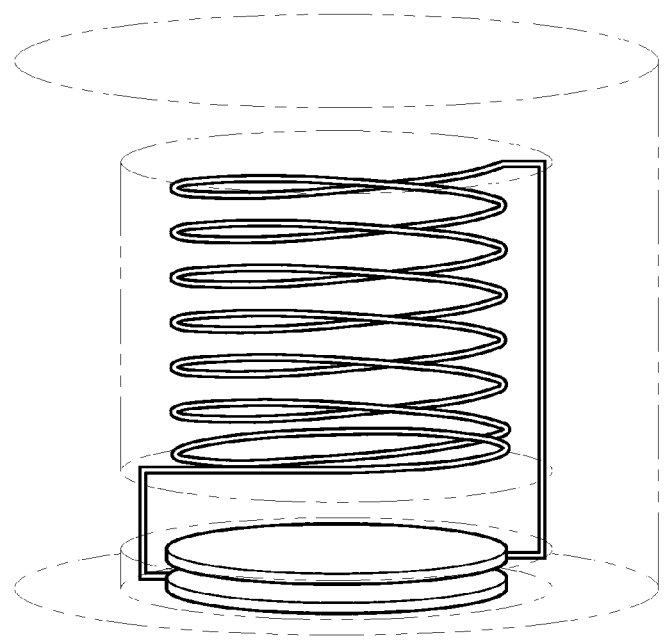
Figure 10:
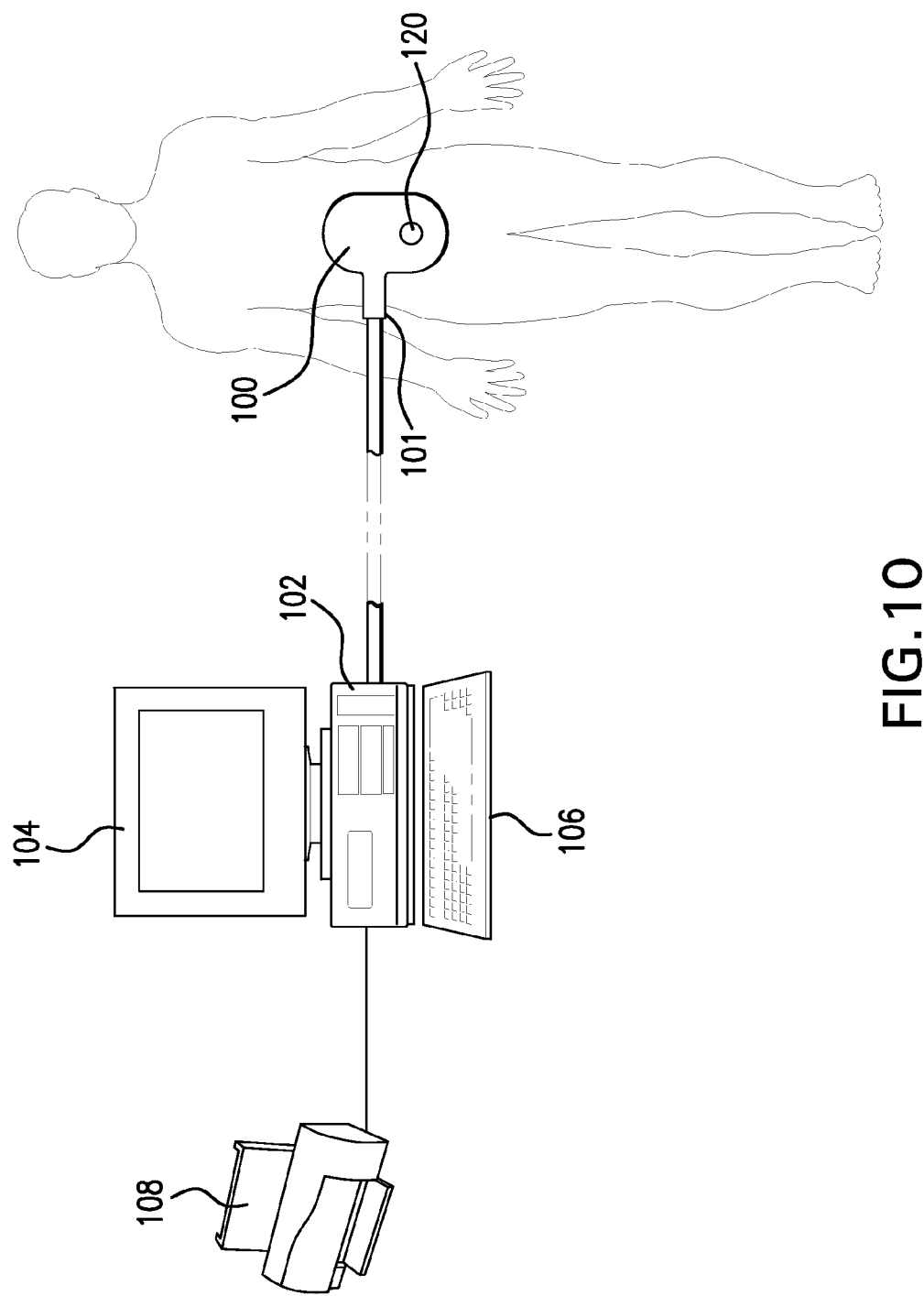

FIG. 9 schematically illustrates a coil inductor of an exemplary LC resonant circuit having a longitudinal axis, FIG. 10 illustrates an exemplary interrogation system for communicating with the first assembly that is positioned within a body.

Figure 11:
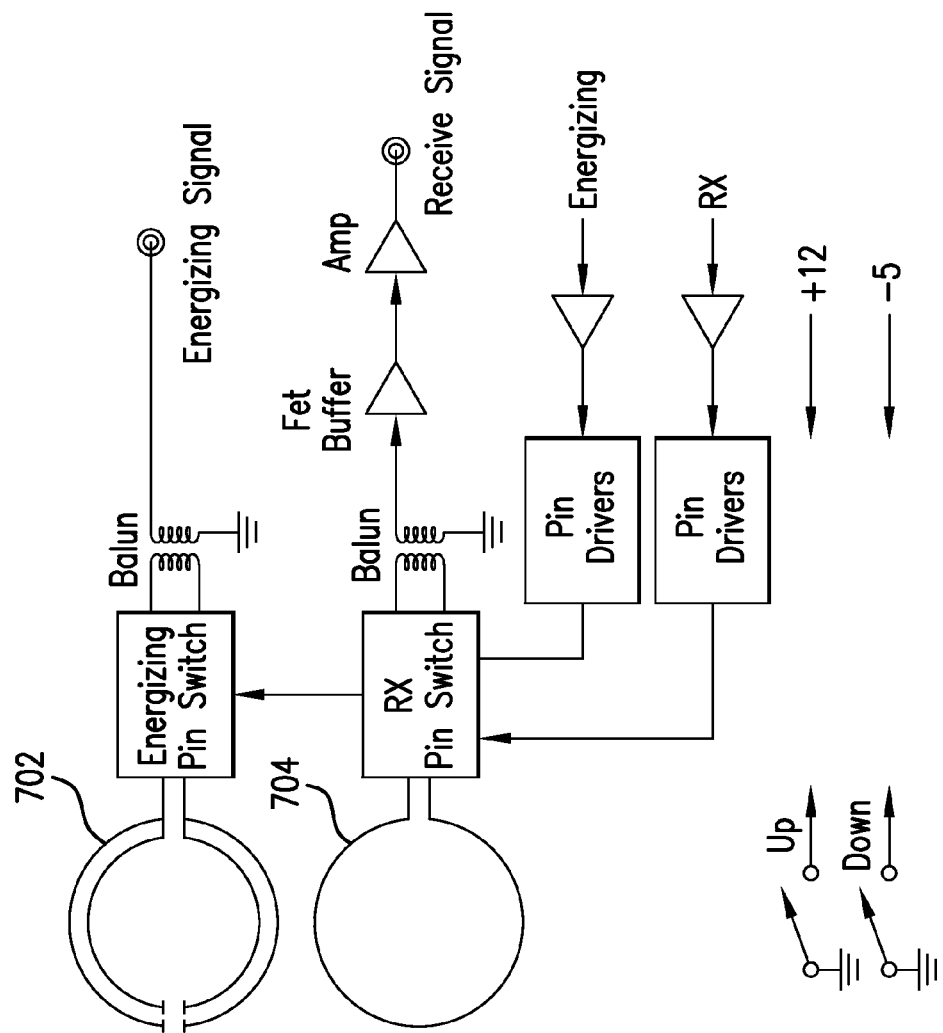

FIG. 11 is an exemplary block diagram of an exemplary coupling loop assembly for communication with a wireless sensor assembly.

FIG. 12A illustrates a exemplary coupling loop that is un-tuned and FIG. 12B illustrates its equivalent circuit.

FIG. 13A illustrates a loop that is tuned and FIG. 13B illustrates its equivalent circuit.

FIG. 14A illustrates a loop terminated into a receiver with a high input impedance and FIG. 14B illustrates its equivalent circuit.

Figure 15:
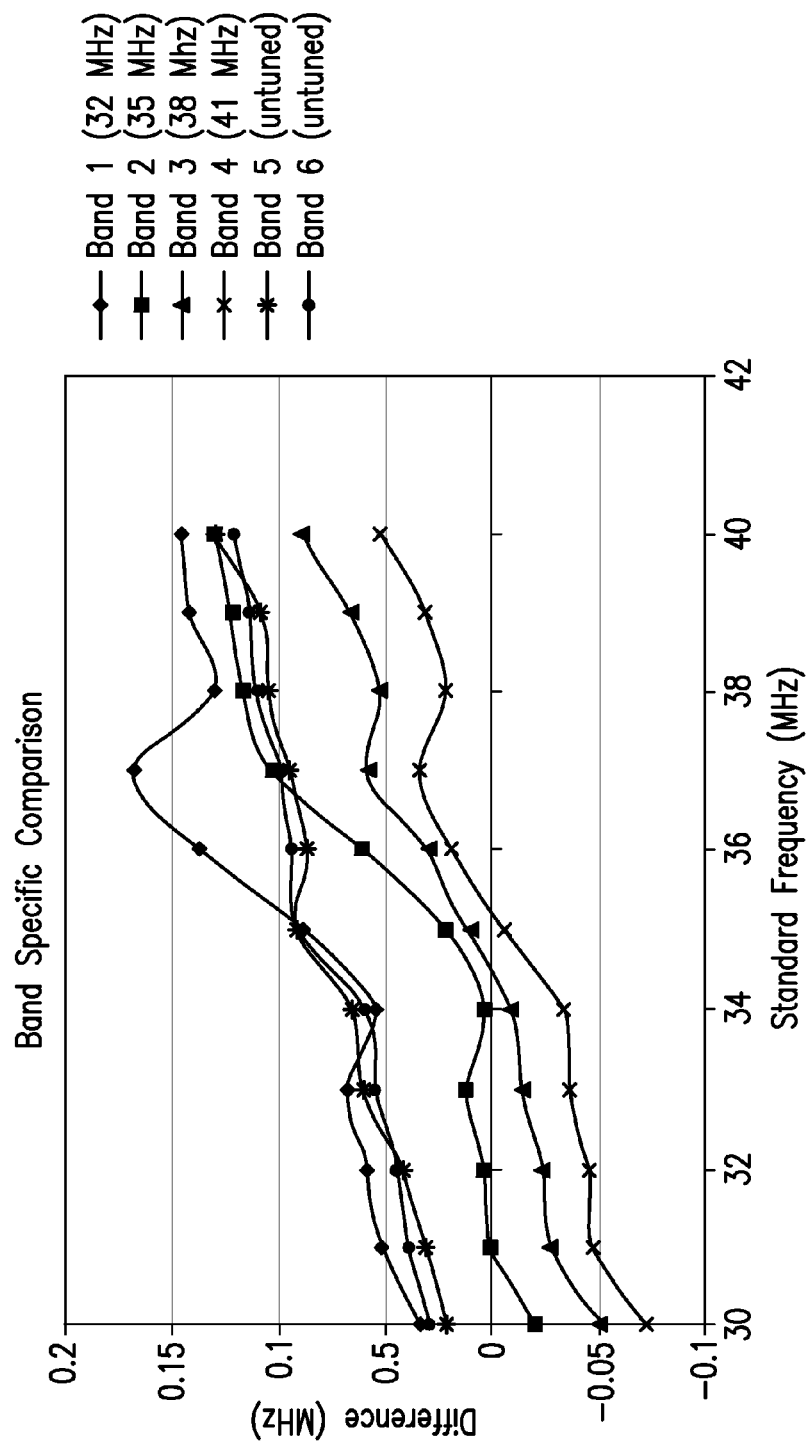

FIG. 15 is a graph that illustrate the comparison of the frequency response for tuned loops and the frequency response for un-tuned loops with high input impedances at the receiver.

Figure 16:
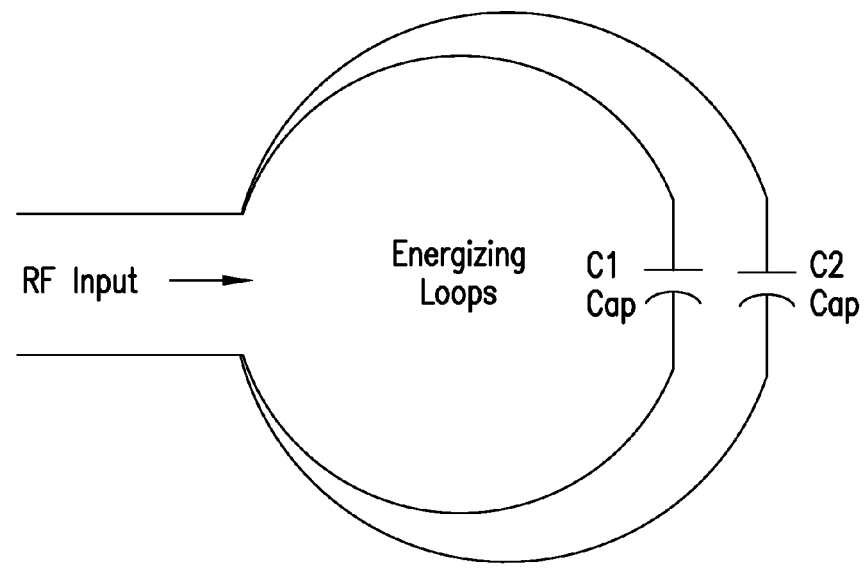

FIG. 16 schematically illustrated two stagger tuned loops.

Figure 17:
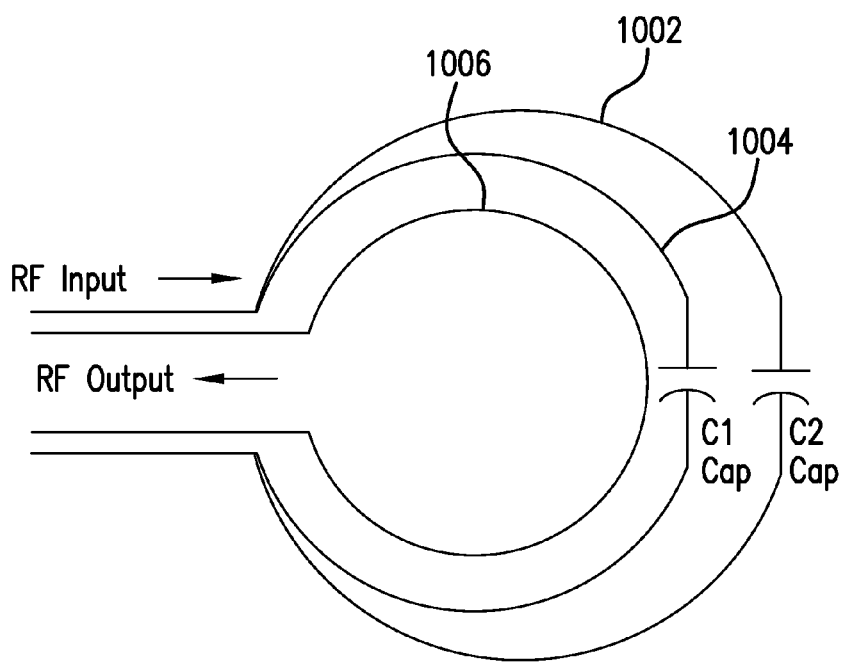

FIG. 17 illustrates the assembly of two stagger-tuned loops 1002, 1004 for transmitting the energizing signal to the passive electrical resonant circuit of the assembly and one un-tuned loop 1006 for receiving the output signal.

DETAILED DESCRIPTION OF THE INVENTION

The present invention can be understood more readily by reference to the following detailed description, examples, drawing, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used throughout, the singular forms "a," "an" and "the" include plural referents unless the context clearly dictates otherwise. Thus, for example, reference to "a sensor assembly" can include two or more such assemblies unless the context indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

Commonly assigned U.S. patent application Ser. Nos. 12/175,803, 11/717,967, 11/613,645, 11/472,905, 11/276, 571, 11/157,375, 11/105,294, and 10/943,772 are incorporated herein by reference in their entirety.

Figure 1:
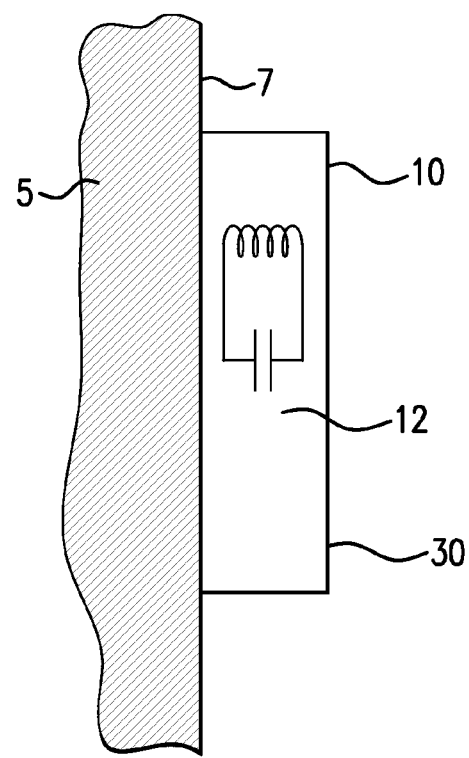
FIG. 1 is a schematic showing an exemplary sensor assembly having a portion of a passive electrical resonant circuit operably coupled to the exterior surface of an implant.
Figure 2:
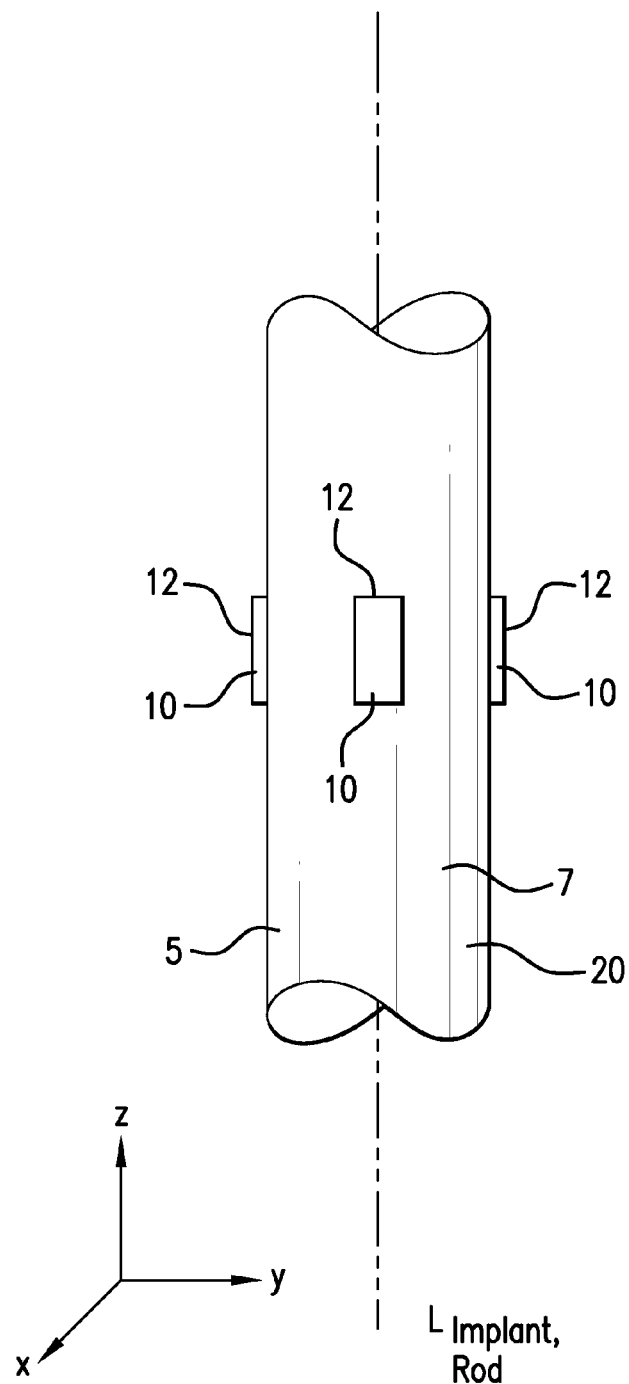
FIG. 2 is a schematic showing a plurality of sensor assembles mounted in a common plane that is transverse to the longitudinal axis of an elongated spinal rod.
Figure 3:
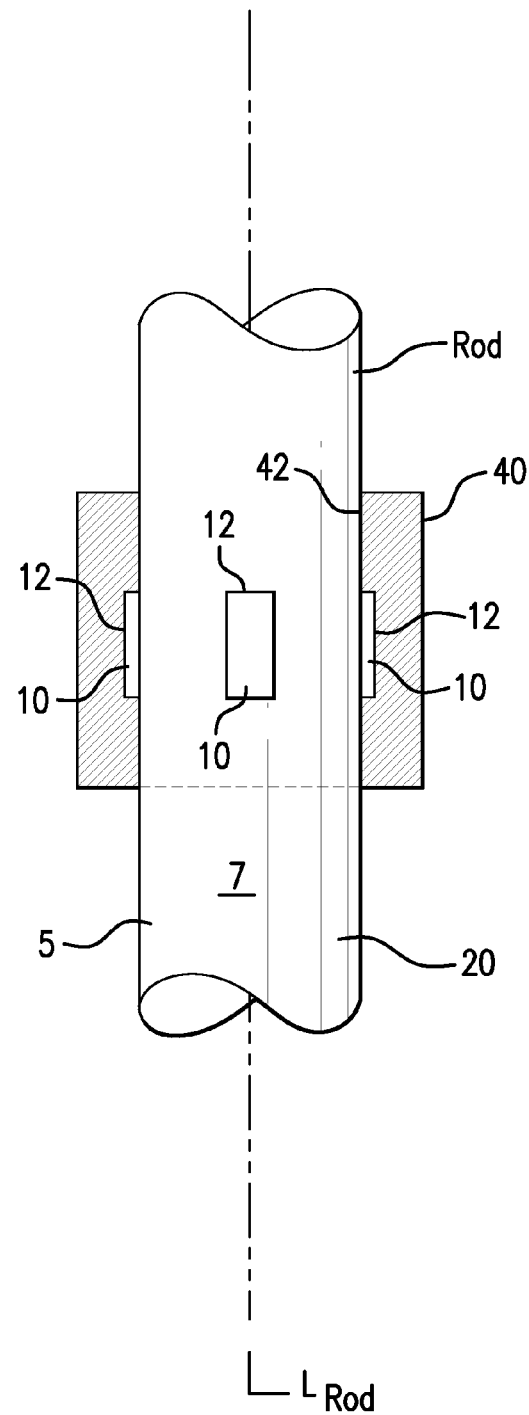
FIG. 3 is a schematic showing sleeve member operable mounted therein an elongated spinal rod, showing a plurality of sensor assemblies mounted on a interior surface of the sleeve member, and showing a portion of a passive electrical resonant circuit of each sensor assembly operably coupled to the exterior surface of an implant.

Embodiments provided herein comprise an apparatus that can be configured to sensing strain on a portion of an implant positioned in a living being. Referring generally to FIGS. 1-3, in one aspect, the apparatus can comprise at least one sensor assembly 10 that can be selectably mountable thereon a portion of the implant. The one sensor assembly comprising a passive electrical resonant circuit 12 that can be configured to be selectively interrogated with RF energy produced by a remote interrogator. The transmitted RF energy can be selected in order to selectively electromagnetically couple the passive electrical resonant circuit. As one will appreciate and as described in more detail below, the remote interrogator can act as an ex-vivo source of desired RF energy. In another aspect, the passive electrical resonant circuit 12, upon energizing via electromagnetic coupling, can be configured to generate an output signal characterized by a frequency that is dependent upon an urged movement of a portion of the passive electrical resonant circuit. The frequency within the output signal is indicative of pressure, force or strain that is applied thereon a portion of the respective sensor assembly. One will appreciate that the output frequency can be the resonant frequency of the sensor assembly. The change in the resonant frequency allows for the system to determine the relative applied pressure, force or strain acting on the portion of the implant.

In one aspect, the resonant frequency change can be used to infer the degree of total load sharing of an exemplary surgical rod/screw implant. For example, a gross change in resonant frequency of the sensor assembly, during a postural change of the patient can indicate that the rod of the implant is subjected to strain upon the change in loading condition. As the bone fusion develops and matures, a similar postural change will result in less stress transmitted to the rod. Thus, a change is load sharing will translate in a proportional change in the strain experienced by the rod, and, in turn, a smaller change in resonant frequency.

In one aspect, the urged movement of a portion of the passive electrical resonant circuit can be between about $10^{-12}$ m to about $10^{-4}$ m, preferably between about $10^{-10}$ m to about $10^{-5}$ m, and more preferably between about $10^{-9}$ m to about $10^{-6}$ m. From the urged movement of the portion of the passive electrical resonant circuit, the strain imposed or applied thereon the portion of the respective sensor assembly can be determined by the system herein to be between about 0.01 to about 10,000 micro-strain, between about 0.10 to about 1000 micro-strain, between about 1 to about 1000 micro-strain, and/or between about 10 to about 1000 micro-strain.

The implant 5 can be any implant that is introduced into the living being and, in one non-limiting example, can comprise a prosthetic device for substantially fixing the relative position of adjacent bones. In another non-limiting example, the implant can comprise an intervertebral cage.

In yet another example, the implant can comprise an elongated spinal rod 20 operably coupled to a plurality of vertebra. In this exemplary aspect, the at least one sensor assembly can be operably coupled to an exterior surface of the rod. In one exemplary aspect, the elongated rod can be formed from a polymeric material such as, for example and without limitation, semi-crystalline thermoplastic polymers. The use of polymeric spinal rods can allow for reduced stress on the screw bones anchor points and construct instrumentation and can potentially accelerate fusion as it allows the vertebrae to compress the graft and promote more bone growth. In another aspect, polymeric rods are transparent to Radio-Frequency (RF) waves, which allow the wireless sensor assemblies to be readily integrated to the surface or within the polymeric spinal rod while being able to communicate with the external interrogator of the system without interferences.

In one aspect, the passive electrical resonant circuit of the sensor assembly can be an electromechanical transducer that is capable of transforming a signal from one form of energy into another, namely from mechanical into electrical energy. In one aspect, it is contemplated that the passive electrical resonant circuit 12 of the sensor assembly 10 can comprise an inductance-capacitance ("LC") resonant circuit. Optionally, in another aspect, the passive electrical resonant circuit 12 of the sensor assembly 10 can comprise a self-resonant inductor circuit.

Conventionally, a passive (no battery) LC resonant circuit is composed of two electrical passive components that are connected in series: (a) a coil, or inductor ("L"), (b) a capacitor ("C"). Such a passive electrical circuit exhibits electrical resonance when subjected to an alternating electromagnetic field. The electrical resonance is particularly acute for a specific frequency value or range of the impinging signal. When the impinging signal substantially reaches the resonant frequency of the LC resonant circuit inside the sensor assembly, a pronounced disturbance of the field can be detected wirelessly. In the simplest approximation, the electrical resonance occurs for a frequency f, related to the value of L and C according to equation 1:

$$f = (2\pi(LC)^{1/2})^{-1} \quad \text{(equation 1)}$$

The passive electrical resonant circuit for the assemblies described herein that utilize a passive electrical resonant circuit can be fabricated, for example and without limitation, via Micro Electro-Mechanical Systems ("MEMS") approach to sensor design, which lends itself to the fabrication of small sensors that can be formed using biocompatible polymers as substrate materials. In a further aspect, appropriately biocompatible coatings can be applied to the surfaces of the respective assemblies in order to prevent adhesion of biological substances to the respective assemblies that could interfere with their proper function. In one example, the passive electrical resonant circuit of the sensor assembly can be manufactured using Micro-machining techniques that were developed for the integrated circuit industry. An example of this type of sensor features an inductive-capacitive (LC) resonant circuit with a variable capacitor is described in Allen et al., U.S. Pat. No. 6,111,520, which is incorporated herein in its entirety by reference. In this sensor, the capacitance varies with the pressure of the environment in which the capacitor is placed. Consequently, the resonant frequency of the exemplary LC circuit of the Allen pressure sensor varies depending on the pressure of the surrounding ambient environment.

As described above, it is contemplated that the LC resonant circuit can comprise a coil inductor operably coupled to a capacitor. In various aspects, the inductance of the LC resonant circuit can be between about 0.1 to about 1000 micro-Henry, preferably between about 1 to about 100 micro-Henry, and more preferably between about 5 to about 15 micro-Henry. The capacitance of the LC resonant circuit can be between about 0.1 to about 1000 pF, preferably between about 0.5 to about 100 pF, and more preferably between about 1 to about 20 pF. The resonant frequency of the LC resonant circuit can be between about 0.1 to about 450 MHz, preferably between about 1 to about 60 MHz, and more preferably between about 25 to about 45 MHz. In addition, the quality factor at self resonance and the frequency range of the self-resonant frequency itself can be between about 5 to 120, preferably between about 5 to about 80, and more preferably between about 10 to about 70.

There are various manufacturing techniques that can be employed to realize sensors assemblies according to the current invention. Capacitors and inductors made by a variety of methods can be manufactured separately, joined through interconnect methods and encapsulated in hermetic packaging. In one embodiment, the strain sensitive capacitor and the three-dimensional inductor coil are formed separately and joined together to form the LC circuit. In another embodiment, the capacitor and inductor coil can be manufactured integral with one another. Additionally, there are several methods to create these discrete elements and to join each discrete element to create the final sensor assembly.

Q factor (Q) is the ratio of energy stored versus energy dissipated. The reason Q is important is that the ring down rate of the sensor assembly is directly related to the Q. If the Q is too small, the ring down rate occurs over a substantially shorter time interval. This necessitates faster sampling intervals, making sensor detection more difficult. Also, as the Q of the sensor increases, so does the amount of energy returned to external electronics. Thus, in one aspect, the sensor assembly can be configured with values of Q sufficiently high enough to avoid unnecessary increases in complexity in communicating with the sensor assembly via external electronics.

The Q of the sensor assembly can be dependent on multiple factors such as, for example and without limitation, the shape, size, diameter, number of turns, spacing between the turns and cross-sectional area of the inductor component. In addition Q will be affected by the materials used to construct the sensor assembly. In one example, the sensor assembly can be formed from materials with low loss tangents to effect a sensor assembly with higher Q factors.

In one aspect, the coil inductor of the LC resonant circuit can be a substantially planar spiral inductor. Optionally, the coil inductor of the LC resonant circuit can have a longitudinal axis and the respective windings of the coil inductor can spiral about and extend along the longitudinal axis.

In one aspect, the inductor coil can be comprised of the inductor coil body and the coil leads. One skilled in the art will appreciate that numerous parameters of the inductor coil can be varied to optimize the balance of size and the electrical properties of the circuit, including the materials, coil diameter, wire gage, number of coil windings, and cross-sectional area of the coil body. Typically, the material of the coil must be highly conductive and also biocompatible. Suitable materials include, but are not limited to, gold, copper and alloys thereof. If the wire is sufficiently strong, the coil can be self-supporting, also known as an "air core" configuration. A solenoid coil is another suitable configuration. If the wire is not sufficiently strong to be unsupported to maintain its intended configuration during assembly and in use, the coil can be formed around a central bobbin comprised of a suitable dielectric material. In the alternative, the wound coil can be encased in a liquid polymer that can cure or otherwise harden after it is applied to the coil body. Polyimide is one preferred material for this application because of its thermal, electrical, and mechanical properties. However, processes achieving substantially similar results that involve lower processing temperatures would make other polymer choices desirable, such choices being obvious to one skilled in the art.

In another aspect, it is contemplated that the at least one sensor assembly 10 can comprise a plurality of sensor assemblies. Relative to the implant, in one aspect, it is contemplated that the plurality of sensor assemblies can be positioned thereon the implant substantially co-planer. In yet another aspect, the plurality of sensors can be positioned in a plane that is substantially transverse to a longitudinal axis of the implant. For example and without limitation, if the implant comprises an elongated rod, the plurality of sensors can be positioned in a plane that is substantially transverse to a longitudinal axis of the elongated rod. Optionally, in this aspect, it is contemplated that the plurality of sensors can be positioned substantially on the X and Y axis of a plane coordinate system that is positioned in the plane that is substantially transverse to the longitudinal axis of the elongated rod.

In yet another aspect, in which the passive electrical resonant circuit of the at least one sensor assembly comprises a LC resonant circuit comprising a coil inductor operably coupled to a capacitor, it is contemplated that the at least one sensor can be positioned to selectively orient the passive electrical resonant circuit of each at least one sensor assembly. In this aspect, it is contemplated that the passive electrical resonant circuit can be oriented thereon the exterior surface of the rod such that the capacitor of the LC resonant circuit can be positioned substantially in a plane that is substantially transverse to a longitudinal axis of the implant. For example, the capacitor of the LC resonant circuit can be positioned substantially in a plane that is substantially transverse to the longitudinal axis of the elongated rod of the implant.

It is contemplated that the passive electrical circuit of the sensor assembly can be housed within a substantially non-permeable enclosure 30 to ensure the protection of the passive electrical circuit of the sensor assembly when the respective sensor assembly is positioned within the living being. In this aspect, the passive electrical circuit of the sensor assembly can be protected from deleterious agents such as corrosion, parasitic excessive strain/stress, biological response, etc. . . . . . As one will appreciate, it is contemplated that the enclosure can be formed of materials that substantially prevent any fluids and/or gases from passing or diffusing through the walls of the enclosure, utilizing manufacturing processes that eliminate undesired holes that could otherwise permit such passing of undesired fluids or gases. In another aspect, the enclosure can be formed of materials that do not allow any fluids and/or gases from passing or diffusing through the walls of the enclosure. Exemplary enclosure material can include, without limitation, biocompatible polymer, such as PEAK, PE, PTFE, FEP and the like, glass, fused-silica, low temperature glass, ceramics, quartz, pyrex, sapphire, sintered zirconia and the like. Optionally, it is also contemplated that the housing can define an internal cavity in which at least a portion of the passive electrical circuitry can be disposed. In a further aspect, a known and invariant quantity of gas can be added to the internal cavity of the housing. In another aspect, it is contemplated that the enclosure can be formed of materials that allow a least a portion of the sensor assembly to flex in response to the relative motion of the portion of the implant that the sensor assembly is coupled thereon. An acceptable level of permeability can be a rate of fluid ingress or egress that changes the original capacitance of the LC circuit by an amount preferably less than 10 percent, more preferably less than 5 percent, and most preferably less than 1 percent over the accumulated time over which measurements will be taken.

In another aspect, the exemplary enclosure materials help to provide the required biocompatibility, non-permeability and/or manufacturing processing capabilities of the sensor assembly. These exemplary materials are considered dielectrics, that is, they are poor conductors of electricity but are efficient supporters of electrostatic or electroquasistatic fields. A dielectric material has the ability to support such fields while dissipating minimal energy. In this aspect, the lower the dielectric loss, the lower the proportion of energy lost, and the more effective the dielectric material is in maintaining high Q.

With regard to operation within the human body, there is a second important issue related to Q, namely that blood and body fluids are conductive mediums and are thus particularly lossy. As a consequence, when a sensor assembly is immersed in a conductive fluid, energy from the sensor assembly will dissipate, substantially lowering the Q and reducing the sensor assembly-to-electronics distance. In one aspect, the loss can be minimized by further separation of the sensor assembly from the conductive liquid, which can be accomplished, for example and without limitation, by coating at least a portion of the sensor assembly in a suitable low-loss-tangent dielectric material.

It various aspects, that the portion of the passive electrical resonant circuit of the at least one sensor assembly 10 can be operably coupled to an exterior surface 7 of the implant 5. In this aspect, it is also contemplated that the portion of the passive electrical resonant circuit of the at least one sensor assembly can be integrally coupled to an exterior surface of the implant. "Coupled" in this sense means that the sensor assembly is mountable onto the implant such that movement of the exterior surface of the transplant will result in a corresponding movement the coupled portion of the passive electrical resonant circuit of the at least one sensor assembly In an alternative embodiment, in which the implant comprises an elongated rod operably coupled to a plurality of vertebra, the apparatus can further comprise a sleeve member 40 that is configured to mount thereon a select portion of the elongated rod 20. In this aspect, the at least one sensor assembly can be coupled to an interior surface 42 of the sleeve member. It is contemplated in this aspect that the portion of the passive electrical resonant circuit of the at least one sensor assembly mounted therein the sleeve member can be positioned into operable coupled contact with a select portion of the exterior surface of the rod when the sleeve member is mounted to the elongated rod. In one exemplary aspect, the sleeve member can be configured to mount to the elongated rod therebetween two pedical screws that are affixed to the adjacent vertebrae.

In one aspect and without limitation, the sleeve member can be made out of electrically conductive or non-conductive material. In another exemplary aspect and without limitation, the sleeve member can be rigid or semi-rigid and can optionally be formed from metal or polymeric materials. In another exemplary aspect, the sleeve member can be made out of a conventional memory shape material that is configured to contract the inner diameter dimension of the sleeve member when the tube reaches body temperature. This contraction serves to fix the sleeve member thereon the exterior surface of the elongated rod. In another aspect, the inner diameter dimension of the sleeve member can be configured to allow the sleeve member to slide over the rod with a desired degree of frictional resistance.

In this aspect, it is contemplated that the at least one sensor assembly mounted therein the sleeve member can comprise a plurality of sensor assemblies. Relative to the implant, in one aspect, it is contemplated that the plurality of sensor assemblies can be positioned thereon the implant substantially co-planer. In yet another aspect, the plurality of sensors therein the sleeve member can be positioned in a plane that is substantially transverse to a longitudinal axis of the implant. For example and without limitation, if the implant comprises an elongated rod, the plurality of sensors therein the sleeve member can be positioned in a plane that is substantially transverse to a longitudinal axis of the elongated rod when the sleeve member is mounted to the rod. Optionally, in this aspect, it is contemplated that the plurality of sensors therein the sleeve member can be positioned substantially on the X and Y axis of a plane coordinate system that is positioned in the plane that is substantially transverse to the longitudinal axis of the elongated rod.

In a further aspect, the strain experienced by a single rod 20 of a spinal implant 5 can, exemplarily and without limitation, range from between about 10 to about 1000 micro-strain, during typical loading or unloading phases as the patient sits downs or stands-up. It is also contemplated that the elongated rod can deform in a variety of ways such as, without limitation, in elongation or compression along the rod longitudinal axis, in rotation about the rod longitudinal axis, in a plane bisecting the rod longitudinal axis. In this aspect, it is contemplated that the respective orientation of the passive resonant electrical circuit can be selected to monitor one or more of the noted deformation paths of the rod.

In one aspect, in an embodiment in which the passive resonant electrical circuit comprises an LC resonant circuit, the portion of the passive electrical resonant circuit of the at least one sensor assembly can be affixed or otherwise coupled to the exterior surface of the rod such that the capacitor plates and the inductor of the LC resonant circuit are oriented substantially parallel to the rod longitudinal axis. In operation, as the rod deforms, so does the portion of the passive electrical resonant circuit of the at least one sensor assembly coupled thereto the rod. As portion of the passive electrical resonant circuit of the at least one sensor assembly deforms, the relative spacing between the respective electrodes of the capacitor is changed, which results in a net change in capacitance value of the capacitor. As a result, the value of the resonant frequency of the sensor assembly's passive resonate electrical circuit formed by the inductor and the capacitor is changed. This change can be detected and determined wirelessly using the system described below.

Figure 4:
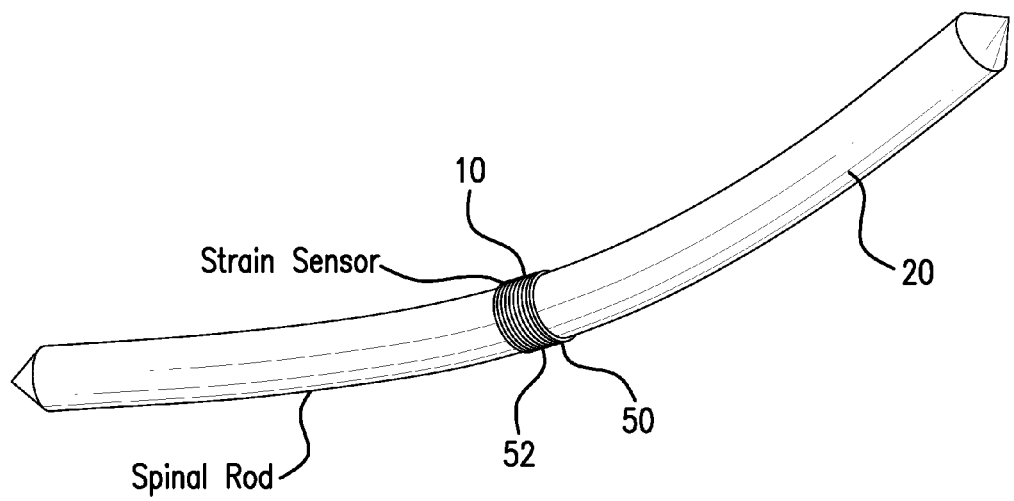
FIG. 4 is a schematic showing a conductive wire wrapped around a select portion of an elongated spinal rod to from a conductive wire coil circuit, and showing the rod under bending loading.
Figure 5:
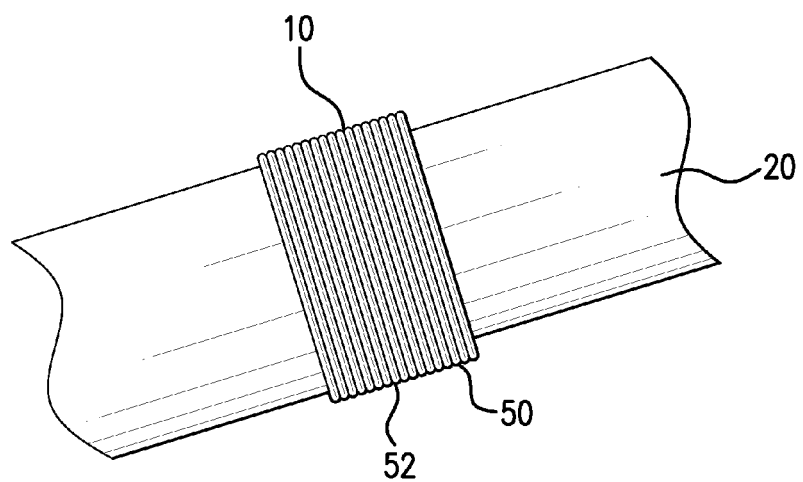
FIG. 5 is an expanded schematic view of FIG. 4.
Figure 6:
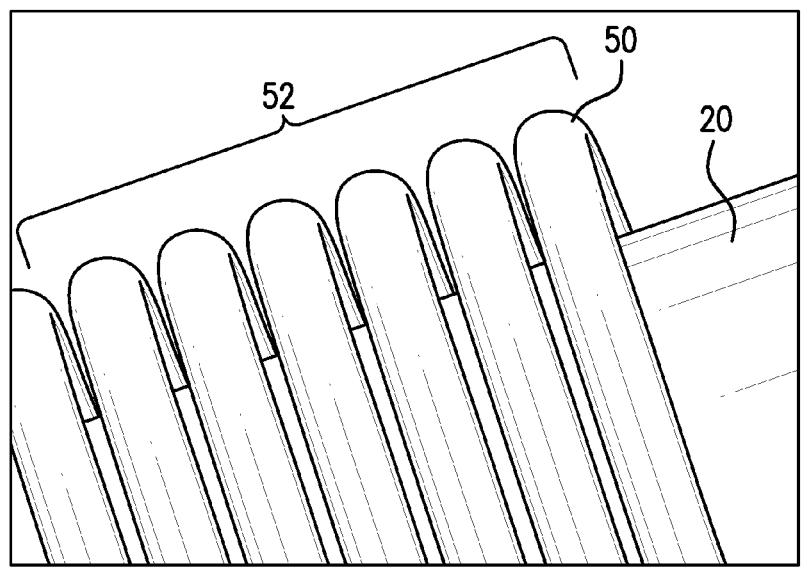
FIG. 6 is an expanded schematic view of FIG. 5. It is contemplated in this aspect that the conductive wire would be in coupled contact with the exterior surface of the rod.

Referring now to FIGS. 4-6, in an alternative embodiment, a conductive wire 50 can be wrapped around a select portion of the elongated spinal rod such that a conductive wire coil circuit 52 is formed that has a self-resonance frequency that is compatible with the frequency detection range of the system interrogator. In optional aspects, the coil can be integrated within the rod, wrapped onto the exterior surface of the elongated rod, or formed within a groove defined therein the exterior surface of the rod. It is contemplated that a wide variety of conventional conductive materials can be used to fabricate the wound coil circuit. In various non-limiting examples, gold, platinum, and the like can be used as it they are an excellent conductor and offers excellent biocompatibility.

In this aspect, wrapping the conductive wire 50 around the spinal rod 20 creates an inductor of inductance L, capacitance C and self-resonance frequency F. The capacitance value of the passive electrical resonant circuit is dependent on the pitch of the formed conductive wire coil circuit. Therefore, in operation, when the elongate spinal rod bends due to external forces that can be applied through the bone screws, the pitch of the coil changes, hence the capacitance value changes and, resultingly, the resonance frequency of the passive electrical resonant circuit changes. The system can detect the change of resonance frequency and can further determine the stress/strain level of the elongate rod based on the relative change in the resonance frequency. As described above, by sensing the stress/strain applied to the elongate rod, bone fusion may be monitored over the course of the treatment protocol, and the healing process may be evaluated not only qualitatively but also quantitatively. In one proposed methodology, it is contemplated that the strain can be monitored periodically over the course of the treatment protocol—any increase in sensed strain over subsequent monitoring periods could be indicative of a possible failure of the fusion surgical protocol. Similarly, continued reductions of the sensed strain can indicate both the success of the fusion surgical protocol as well as the relative degree of bone fusion occurring therebetween the respective adjoining vertebrae.

In various aspects, the inductance of the conductive wire coil circuit can be between about 0.1 to about 1000 micro-Henry, preferably between about 1 to about 100 micro-Henry, and more preferably between about 5 to about 15 micro-Henry. The capacitance of the conductive wire coil circuit can be between about 0.1 to about 1000 pF, preferably between about 0.5 to about 100 pF, and more preferably between about 1 to about 20 pF. The resonant frequency of the conductive wire coil circuit can be between about 0.1 to about 450 MHz, preferably between about 1 to about 60 MHz, and more preferably between about 25 to about 45 MHz. In addition, the quality factor at self resonance and the frequency range of the self-resonant frequency itself can be between about 5 to 120, preferably between about 5 to about 80, and more preferably between about 10 to about 70.

As one skilled in the art will further appreciate, the wire gage, coil diameter, cross-sectional area of the coil body, and number of windings all influence the value of inductance and the detection range of the circuit. As any of these properties increase, so do the size and the inductance of the coil, as well as the sensor-to-electronics distance. To specify an inductor coil for use in the sensor assembly, size considerations must be balanced with those of inductance and Q.

As described above, in one embodiment, the sensor assembly comprises a passive LC resonant circuit with a varying capacitor. Because the sensor assembly can be fabricated using completely passive electrical components and has no active circuitry, it does not require on-board power sources such as batteries, nor does it require leads to connect to external circuitry or power sources. These features create a sensor assembly which is self-contained within the enclosure and lacks physical interconnections that traverse the hermetic enclosure or housing.

In one exemplary aspect, the capacitor in the portion of the passive electrical resonant circuit of the at least one sensor assembly can comprises at least two conductive elements separated by a gap. In operation, if an external force is exerted on the sensor assembly, the coupled portion of the passive electrical resonant circuit of the sensor assembly having the at least two conductive elements separated by a gap can deflect, which can change the relative position between the at least two conductive elements. This movement has the effect of changing the gap between the conductive elements, which will consequently change the capacitance of the LC resonant circuit. As noted above, such an exemplary LC resonant circuit is a closed loop system whose resonance is proportional to the inverse square root of the product of the inductor and capacitor. Thus, changes in strain applied to the sensor assembly alter the capacitance and, ultimately, cause a shift in the resonant frequency of the sensor assembly. In one aspect, the pressure or strain being induced thereon the sensor assembly by the attached portion of the implant can then determined by referencing the value obtained for the resonant frequency to a previously generated curve relating resonant frequency to strain.

Because of the presence of the inductor in the LC resonant circuits described herein, it is possible to couple to the sensor assembly electromagnetically and to induce a current in the LC resonant circuit via a magnetic loop. This characteristic allows for wireless exchange of electromagnetic energy with the sensor assembly and the ability to operate it without the need for an on-board energy source such as a battery. Thus, using the system described herein, it is possible to determine the pressure or strain applied to the sensor assembly by a simple, non-invasive procedure by remotely interrogating the sensor assembly, detecting and recording the resonant frequency, and converting this value to a strain or stress measurement.

In a further aspect, the system for sensing strain on a portion of an implant positioned in a living being of embodiments described herein can comprises an ex-vivo source of RF energy and the at least one sensor assembly described above. In one aspect, the at least one sensor assembly can comprises a passive electrical resonant circuit positioned within the living being that is configured to be selectively electromagnetically coupled to the ex-vivo source of RF energy. The sensor can be configured to generate an output signal characterized by a frequency that is dependent upon urged movement of a portion of the passive electrical resonant circuit in response to the electromagnetic coupling. In another aspect, the system can comprise a non-implantable remotely operated receiver that is configured for receiving the output signal indicative of strain applied thereon the portion of the passive electrical resonant circuit of the at least one sensor assembly. In a further aspect, the system further comprising means for calibrating the at least one sensor assembly.

In a further aspect, the system comprises a means for monitoring the output signal, which frequency can be the resonant frequency of the sensor assembly. In one exemplary aspect, the means for monitoring the output signal produced by the sensor assembly can comprise a means for detecting or otherwise receiving the output signal of the sensor assembly and a processor, or similar processing means, that can be configured to determine the relative distance between the respective first and second assemblies based on the received and sensed resonant frequency of the sensor assembly.

In another aspect, the system described herein provides for a system capable of determining the resonant frequency and bandwidth of the sensor assembly using an impedance approach. In this approach, an excitation signal can be transmitted using a transmitting antenna to electromagnetically couple the sensor assembly having a passive electrical resonant circuit to the transmitting antenna, which resultingly modifies the impedance of the transmitting antenna. The measured change in impedance of the transmitting antenna allows for the determination of the resonant frequency and bandwidth of the passive electrical resonant circuit of the sensor assembly.

In a further aspect, the system described herein provides for a transmit and receive interrogation system configured to determine the resonant frequency and bandwidth of a resonant circuit within a particular sensor assembly. In this exemplary process, an excitation signal of white noise or predetermined multiple frequencies can be transmitted from a transmitting antenna and the passive electrical resonant circuit of the sensor assembly is electromagnetically coupled to the transmitting antenna. Current is induced in the passive electrical resonant circuit of the sensor assembly as it absorbs energy from the transmitted excitation signal, which results in the oscillation of the passive electrical circuit at its resonant frequency. A receiving antenna, which can also be electromagnetically coupled to the transmitting antenna, receives the excitation signal minus the energy which was absorbed by the assembly. Thus, the power of the received or output signal experiences a dip or notch at the resonant frequency of the assembly. The resonant frequency and bandwidth can be determined from this notch in the power. In one aspect, the transmit and receive methodology of determining the resonant frequency and bandwidth of a passive electrical resonant circuit of an assembly can include transmitting a multiple frequency signal from a transmitting antenna to electromagnetically couple the passive electrical resonant circuit on the sensor assembly to the transmitting antenna in order to induce a current in the passive electrical resonant circuit of the sensor assembly. A modified transmitted signal due to the induction of current in the passive electrical circuit is received and processed to determine the resonant frequency and bandwidth and subsequently process to determine the applied strain.

In another aspect, the system can determine the resonant frequency and bandwidth of a passive electrical resonant circuit within a particular sensor assembly by using a chirp interrogation system, which provides for a transmitting antenna that is electromagnetically coupled to the resonant circuit of the assembly. In this aspect, an excitation signal of white noise or predetermined multiple frequencies can be applied to the transmitting antenna for a predetermined period of time to induce a current in the passive electrical resonant circuit of the sensor assembly at the resonant frequency. The system then listens or otherwise receives an output signal that radiates from the energized passive electrical resonant circuit of the assembly. In this aspect, the resonant frequency and bandwidth of the passive electrical resonant circuit are determined from the output signal. In this aspect, the chirp interrogation method can include transmitting a multi-frequency signal pulse from a transmitting antenna; electromagnetically coupling a passive electrical resonant circuit on a sensor assembly to the transmitting antenna to induce a current in the resonant circuit; listening for and receiving a output signal radiated from the energized passive electrical circuit of the sensor assembly; determining the resonant frequency and bandwidth from the output signal, and subsequently processes the resonant frequency and bandwidth to determine the applied strain.

In a further aspect, the system described herein can provide an analog system and method for determining the resonant frequency of a passive electrical resonant circuit within a particular sensor assembly. The analog system can comprise a transmitting antenna coupled as part of a tank circuit, which, in turn, is coupled to an oscillator. In this aspect, a signal is generated which oscillates at a frequency determined by the electrical characteristics of the tank circuit. The frequency of this signal is further modified by the electromagnetic coupling of the passive electrical resonant circuit of the assembly. This signal can be applied to a frequency discriminator that provides a signal from which the resonant frequency of the resonant circuit is determined. In this aspect, the analog method can include generating a transmission signal using a tank circuit that includes a transmitting antenna; modifying the frequency of the transmission signal by electromagnetically coupling the passive electrical resonant circuit of the assembly to the transmitting antenna, and converting the modified transmission signal into a standard signal for further application.

One exemplary method of sensor assembly interrogation is explained in more detail in commonly assigned U.S. patent application Ser. No. 11/105,294. In the described methodology, the interrogating system energizes the sensor with a low duty cycle, gated burst of RF energy having a predetermined frequency or set of frequencies and a predetermined amplitude. The energizing signal is coupled to the passive electrical resonant circuit via a magnetic loop. The energizing signal induces a current in the passive electrical resonant circuit that is maximized when the frequency of the energizing signal is substantially the same as the resonant frequency of the passive electrical resonant circuit. The system receives the ring down response of the sensor assembly via magnetic coupling and determines the resonant frequency of the sensor assembly, which is then used to determine the measured strain applied thereon the sensor assembly. In one aspect, the resonant frequency of the sensor assembly is determined by adjusting the frequency of the energizing signal until the phase of the ring down signal and the phase of a reference signal are equal or at a constant offset. In this manner, the energizing signal frequency is locked to the sensor assembly's resonant frequency and the resonant frequency of the sensor assembly is known. The strain applied to the sensor assembly by the implant can then be ascertained.

In one aspect, the system can comprise a coupling loop that can be selectively positioned relative to the at least one sensor assembly to maximize the electromagnetic coupling between the passive electrical resonant circuit of the assembly and the coupling loop. The system can also provide the necessary isolation between the energizing signal and the output signal. In one aspect, it is contemplated that the system can energize the passive electrical resonant circuit of the sensor assembly with a low duty cycle, gated burst of RF energy having a predetermined frequency or set of frequencies and a predetermined amplitude. The energizing signal is electromagnetically coupled to the passive electrical resonant circuit of the sensor assembly via one or more energizing loops. In operation, each energizing loop can be tuned to a different resonant frequency. The selection of the desired resonant frequencies can be based on the desired bandwidth, which, in one non-limiting exemplary aspect, can range between about 30 to about 37.5 MHz.

The energizing signal induces a current in the passive electrical resonant circuit of the sensor assembly that is maximized when the energizing frequency is the same as the resonant frequency of the passive electrical resonant circuit of the assembly. The system receives the ring down response of the assembly (or assemblies) via one or more coupling loops and determines the resonant frequency of the sensor assembly, which can be used to determine the strain applied to the sensor assembly.

In one aspect, a pair of phase locked loops ("PLLs") can be used to adjust the phase and the frequency of the energizing signal until its frequency locks to the resonant frequency of the passive electrical resonant circuit of the assembly. In one embodiment, one PLL samples during the calibration cycle and the other PLL samples during the measurement cycle. In one non-limiting example, these cycles can alternate every 10 microseconds and can be synchronized with the pulse repetition period. In one aspect, the calibration cycle adjusts the phase of the energizing signal to a fixed reference phase to compensate for any system delay or varying environmental conditions. The environmental conditions that can affect the accuracy of the reading can include, but are not limited to, proximity of reflecting or magnetically absorbative objects, variation of reflecting objects located within transmission distance, variation of temperature or humidity which can change parameters of internal components, and aging of internal components.

In one aspect, one of the PLLs can be used to adjust the phase of the energizing signal and is referred to herein as the fast PLL. The other PLL can be used to adjust the frequency of the energizing signal and is referred to herein as the slow PLL. During the time that the energizing signal is active, a portion of the signal enters the receiver and is referred to herein as a calibration signal. The calibration signal is processed and sampled to determine the phase difference between its phase and the phase of a local oscillator. The cycle in which the calibration signal can be sampled is referred to as the calibration cycle. In one aspect, the system can adjust the phase of the energizing signal to drive the phase difference to zero or another select reference phase.

During the measurement cycle, the signal coupled from the passive electrical resonant circuit of the sensor assembly (referred to herein as the output signal) can be processed and sampled to determine the phase difference between the output signal and the energizing signal. The system can then adjust the frequency of the energizing signal to drive the phase difference to zero or other reference phase. Once the slow PLL is locked, the frequency of the energizing signal is deemed to match the resonant frequency of the passive electrical resonant circuit of the sensor assembly. The operation of the slow PLL is qualified based on signal strength so that the slow PLL does not lock unless the strength of the output signal meets a predetermined signal strength threshold.

In one aspect, a single un-tuned coupling loop can be is used. In this exemplary aspect, the loop can be connected to an input impedance that is high relative to the loop inductance. Optionally, multiple coupling loops can be used and each loop is tuned to a different resonant frequency.

In another aspect, the loops can be connected to a base unit that generates the energizing signal and processes the output signal via a cable assembly. In this aspect, the cable assembly provides isolation between the energizing signal and the output signal by maximizing the distance between the coaxial cables that carry the signals and maintaining the relative positions of the coaxial cables throughout the cable assembly. In another exemplary aspect, the coaxial cables can be positioned on opposite sides of an internal cable, approximately 180 degrees apart. Shielding can also be used to isolate the energizing signal from the output signal. In one aspect, it is contemplated that additional shielding can be provided around each of the respective coaxial cables.

In one aspect, FIG. 10 illustrates an exemplary interrogation system for communicating with the wireless apparatus described above that is positioned within a body. Without limitation, it is contemplated that the system can be used in at least two environments: the operating room during implant and the physician's office during follow-up examinations.

In one exemplary embodiment, the interrogation system can comprise a coupling loop 100, a base unit 102, a display device 104, and an input device 106, such as, for example and without limitation, a keyboard. In one exemplary embodiment, the base unit can include an RF amplifier, a receiver, and signal processing circuitry. In one aspect, the coupling loop 100 can be configured to charge the passive electrical resonant circuit of the sensor assembly and then couple output signals from the energized passive electrical resonant circuit of the sensor assembly into the receiver. Schematic details of the exemplary circuitry are illustrated in Figure X.

The display 104 and the input device 106 can be used in connection with the user interface for the system. In the embodiment illustrated in FIG. 10, the display device and the input device are conventionally connected to the base unit. In this embodiment, the base unit can also provides conventional computing functions. In other embodiments, the base unit can be connected to a conventional computer, such as a laptop, via a communications link, such as an RS-232 link. If a separate computer is used, then the display device and the input devices associated with the computer can be used to provide the user interface. In one embodiment, LABVIEW software can be used to provide the user interface, as well as to provide graphics, store and organize data and perform calculations for calibration and normalization. The user interface can record and display patient data and guide a user through surgical and follow-up procedures. In another aspect, an optional printer 108 can be operably connected to the base unit and can be used to print out patient data or other types of information. As will be apparent to those skilled in the art in light of this disclosure other configurations of the system, as well as additional or fewer components can be utilized with embodiments of the invention.

In one embodiment, the coupling loop can be formed from a band of copper. In this aspect, it is contemplated that the coupling loop comprises switching and filtering circuitry that is enclosed within a shielded box. In this aspect, the loop can be configured to charge the passive electrical resonant circuit of the assembly and then couples signals from the energized passive electrical resonant circuit of the assembly sensor into a receiver. It is contemplated that the antenna can be shielded to attenuate in-band noise and electromagnetic emissions.

In an alternative embodiment for a coupling loop, as shown in FIG. 11, separate loops for energizing 702 and for receiving 704 are provided, although a single loop can be used for both functions. PIN diode switching inside the loop assembly can be used to provide isolation between the energizing phase and the receive phase by opening the RX path pin diodes during the energizing period, and opening the energizing path pin diodes during the coupling period. It is contemplated in this embodiment that multiple energizing loops can be staggered tuned to achieve a wider bandwidth of matching between the transmit coils and the transmit circuitry.

In one aspect, the coupling loop or antenna can provide isolation between the energizing signal and the output signal, support sampling/reception of the output signal soon after the end of the energizing signal, and minimize switching transients that can result from switching between the energizing and the coupled mode. The coupling loop can also provide a relatively wide bandwidth, for example from between about X to about Y and preferable from between about 30 to about 37.5 MHz.

In one embodiment, separate loops can be used for transmitting the energizing signal to the passive electrical resonant circuit of the sensor assembly and coupling the output signal from the energized passive electrical resonant circuit of the sensor assembly. Two stagger-tuned loops can be used to transmit the energizing signal and an un-tuned loop with a high input impedance at the receiver can be used to receive the output signal. The term "coupling loop" is used herein to refer to both the loop(s) used to receive the output signal from the energized passive electrical resonant circuit of the sensor assembly (the "assembly coupling loop"), as well as the loop assembly that includes the loop(s) used to transmit the energizing signal to the passive electrical resonant circuit of the sensor assembly (the "energizing loop") and the sensor assembly coupling loop(s).

During the measurement cycle, the assembly coupling loop can be configured to couple the output signal from the energized passive electrical resonant circuit of the sensor assembly, which is relatively weak and dissipates quickly. In one aspect, the voltage provided to the receiver in the base unit depends upon the design of the assembly coupling loop and in particular, the resonant frequency of the loop.

In a further aspect, it is contemplated that the coupling loop can be un-tuned or tuned. FIG. 12A illustrates a loop that is un-tuned and FIG. 12B illustrates its equivalent circuit. The loop has an inductance, $L_1$, and is terminated into the receiver using a common input impedance, which can, for example and without limitation, be 50 ohms. The voltage at the receiver, $V_1$, is less than the open circuit voltage of the loop, i.e., the voltage that would be coupled by the loop if the loop was not terminated, $V_s$, and can be calculated as shown below.

$$V_1 = V_s \frac{50}{50 + j\omega L_1} \quad \text{Equation 2}$$

Where L1 is the inductance of the loop and $\omega=2\pi f$, with f=frequency in hertz.

To maximize the voltage at the receiver, it is contemplated that the loop can be tuned. FIG. 13A illustrates a loop that is tuned and FIG. 13B illustrates its equivalent circuit. In this aspect, the loop has an inductance, $L_1$, and a capacitance, $C_1$. The capacitance, $C_1$, is selected so that it cancels the inductance, $L_1$ at the resonant frequency, i.e., the series resonant circuit, $C_1$-$L_1$, is 0 ohms at the resonant frequency. At the resonant frequency the voltage at the receiver, $V_1$, equals the voltage coupled by the loop, $V_s$. One disadvantage of this type of loop is that it is optimized for a single frequency. If the loop is used in an environment where the frequency of the output signal is changing, then the capacitance is either changed dynamically or set to a compromise value (e.g., the loop is tuned to a single frequency within the band of interest).

To minimize this issue, another embodiment illustrated in FIGS. 14A and 14B uses an un-tuned loop with a high input impedance at the receiver. FIG. 14A illustrates a loop terminated into a receiver with a high input impedance and FIG. 14B illustrates its equivalent circuit. In this aspect, the input impedance at the receiver is selected so that the energy lost due to the loop impedance, $L_1$, is relatively insignificant. Using Zin as the input impedance at the receiver, the voltage at the receiver, $V_1$, is calculated as shown below.

$$V_1 = V_s \frac{Zin}{Zin + j\omega L_1} \quad \text{Equation 3}$$

Since Zin is much larger than $j\omega L_1$, this can be approximated by the following equation $$V_1 = V_s \frac{\infty}{\infty + j\omega L_1}, \text{ or } V_1 = V_s \quad \text{Equation 4}$$

As shown by the foregoing equation, the use of a relatively high input impedance at the input of the receiver negates $L_1$ for all frequencies. In one embodiment, a high impedance buffer can be inserted between the loop and an exemplary 50 ohm receiver circuit. In this embodiment, the high impedance buffer is on the order of 1 Mohm while the impedance of the loop is on the order of 200 ohms. In other embodiments, it is contemplated that the input impedance is at least two times the loop impedance.

In one aspect, the frequency response within the band of interest is more monotonic if the assembly coupling loop uses a high input impedance at the receiver, than if a tuned loop is used with a 50 ohm input impedance. FIG. 15 compares the frequency response for tuned loops and the frequency response for un-tuned loops with high input impedances at the receiver. The y-axis represents the difference in measured frequency between a calibration system using a network analyzer and the loop. The x-axis represents the frequency of the L-C standard used in the measurements. Linear interpolation was used between measurement points. Band 1 corresponds to a loop resonant at 32 MHz, Band 2 corresponds to a loop resonant at 35 MHz, Band 3 corresponds to a loop resonant at 38 MHz, and Band 4 corresponds to a loop resonant at 41 MHz. Bands 1-4 correspond to a prior art design that uses switched capacitors banks to vary the loop resonance to achieve the needed bandwidth. Bands 5 and 6 correspond to un-tuned loops.

Bands 1-4 illustrate a slope variation within the band of interest, which can affect the accuracy of measurements made using the loop. Bands 5 and 6 illustrate that the variation within the band of interest is less than in the systems using a tuned loop. The more monotonic frequency response of an un-tuned loop with a high input impedance requires a simpler set of calibration coefficients to be used for the frequency conversion calculation.

An alternative embodiment to using an un-tuned loop and a high input impedance is to use stagger-tuned loops. If stagger tuned loops are used to receive the output signal, then the loops can be tuned in a manner similar to that described in the following paragraphs in connection with the transmission of an energizing signal.

During the energizing mode, the energizing loop produces a magnetic field. The intensity of the magnetic field produced by the energizing loop depends, in part, on the magnitude of the current within the loop. In one aspect, the current is maximized at the energizing frequency if the impedance of the loop is essentially 0 ohms at the energizing frequency. The resonant frequency of the loop is related to the loop inductance and capacitance, as shown below.

$$f_o = \frac{1}{2\pi\sqrt{L*C1}} \quad \text{Equation 5}$$

The impedance of the loop is preferably 0 ohms over the frequency range of interest, which, in an exemplary operating environment, can be, without limitation, between about 30 MHz to about 37.5 MHz. To achieve the desired impedance over the desired frequency range, two or more loops can be stagger tuned as exemplarily shown in FIG. 16.

The resonant frequencies for the loops are based on the bandwidth of interest. If there are two loops, then the loops can be spaced geometrically. In one exemplary non-limiting aspect, the resonant frequency of the first loop is can be about 31 MHz and the resonant frequency of the second loop can be about 36.3 MHz, which corresponds to the pole locations of a second order Butterworth bandpass filter having about −3 dB points at about 30 MHz and about 37.5 MHz. Although FIG. 16 illustrates two loops, it is contemplated that other embodiments can use a different number of loops, which provides coverage for a much wider frequency range. In one aspect, the loops can be spaced logarithmically if there are more than two loops.

FIG. 17 illustrates the assembly of two stagger-tuned loops 1002, 1004 for transmitting the energizing signal to the passive electrical resonant circuit of the sensor assembly and one un-tuned loop 1006 for receiving the output signal. In this aspect, the loops are parallel to one another with the un-tuned loop inside the stagger-tuned loops. Placing the loop used to receive the output signal inside of the loops used to transmit the energizing signal helps to shield the output signal from environmental interferences. In one embodiment, the loops can be positioned within a housing.

One will appreciate that the signal from an implanted passive sensor assembly is relatively weak and is attenuated by the surrounding tissue and the distance between the assembly and the coupling loop. Optimizing the position and angle of the coupling loop relative to the assembly can help maximize the coupling between the assembly and the coupling loop. In one aspect, the coupling loop can be positioned so that a plane defined by the assembly coupling loop is approximately parallel to the inductor within the passive electrical resonant circuit of the sensor assembly and the sensor assembly is approximately centered within the sensor coupling loop. If the coupling loop is not positioned in this manner relative to the inductor, then the strength of the output signal is reduced by the cosine of the angle between the sensor coupling loop and the inductor of the resonant circuit.

In yet another aspect, orientation features can be provided for positioning the coupling loop relative to at least the sensor assembly to maximize the coupling between the sensor assembly and the coupling loop. In one aspect, the orientation features can facilitate the placement of the respective sensor assemblies during implantation and the placement of the coupling loop during follow-up examinations. In one aspect, the sensor assembly and the coupling loop can include orientation features that are visible using conventional medical imaging technology. In exemplary aspects, the orientation features on the at least one sensor assembly can include radiopaque markings and the orientation features on the coupling loop can include a pattern in the ribbing of the housing for the loop.

In one exemplary aspect, to facilitate the proper coupling of the system, the sensor assembly, the sensor assembly housing or enclosure, and/or the implant can include orientation features, which are visible using a medical imaging technology, such as fluoroscopy, to facilitate the placement of the at least one sensor assembly during implantation and the coupling loop during follow-up examinations. To position the coupling loop relative to the sensor assembly, the coupling loop is moved or adjusted until a predetermined pattern appears. In one aspect, the orientation features on the coupling loop can be implemented as a pattern in the ribbing of the housing for the loop, which aids in positioning the coupling loop relative to the assembly of the implant. In one aspect, the housing includes an essentially circular section that can be smaller than the diameter of section. When assembled, the sensor coupling and energizing loops are positioned within the ring-shaped section. The orientation features are located in the circular section.

To receive an output signal from the sensor assembly, the physician positions the coupling loop so that the sensor assembly is positioned approximately at the center of the coupling loop and the angle of the coupling loop is adjusted until the desired orientation of the passive electrical resonant circuit of the sensor assembly and the coupling loop is achieved, which places the inductor coil within the passive electrical resonant circuit essentially parallel to the coupling loop. In one aspect, the orientation feature on the sensor assembly can aid in positioning the coupling loop so that the sensor is at approximately the center of the loop.

In one aspect, isolation of the energizing signal and the output signal provided by the base unit and the coupling loop can be maintained in the cable that connects the base unit to the coupling loop. In one aspect, a cable can connect the base unit to the coupling loop and isolate the energizing signal from the output signal. In one aspect, the distal end of the cable that connects to the base unit can comprise a multi-pin connector (e.g., AL06F15-ACS provided by Amphenol) and a right angle housing. The proximal end of the cable that connects to the coupling loop can comprise a first connector, which can be a multi-pin connector (e.g., AMP 1-87631-0 provided by Amphenol) that operably connects to the filtering and switching circuitry associated with the loop; a second connector that operably connects to the energizing loop; and a third connector that operably connects to the loop that couples the signal from the sensor. In this exemplary aspect, the right angle housing and the strain relief provide strain relief at the respective ends of the cable. When assembled with the housing, the strain relief can be positioned proximate to the housing. Optionally, other types of strain relief can be implemented, including, without limitation, physical constraints, such as tie wraps, ferrals or epoxy, and/or service loops. In one aspect, the cable can also comprise ferrite beads, which can help reduce ground currents within the cable.

In one aspect, the position of the coaxial cables within the cable is designed to maximize the isolation between the energizing signal and the output signal, while minimizing the diameter of the cable. The cable is configured to maximize the isolation between the coax cable that transmits the energizing signal and the inner bundle and the twisted pairs and the coax cable that receives the output signal and the inner bundle.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed hereinabove, and that many modifications and other embodiments are intended to be included within the scope of the appended claims. Moreover, although specific terms are employed herein, as well as in the claims which follow, they are used only in a generic and descriptive sense, and not for the purposes of limiting the described invention, nor the claims which follow.

What is claimed is:

1. An apparatus for sensing strain on a portion of an implant positioned in a living being, the apparatus comprising:
   at least one sensor assembly mountable thereon a portion of the implant and comprising a passive electrical resonant circuit, wherein the at least one sensor assembly is configured to be selectively electromagnetically coupled to an ex-vivo source of RF energy, and wherein, in response to the electromagnetic coupling, each sensor assembly is configured to generate an output signal characterized by a frequency that is dependent upon urged movement of a portion of the passive electrical resonant circuit between about $10^{-12}$ m to about $10^{-4}$ m and is indicative of strain applied thereon the portion of the passive electrical resonant circuit of the respective sensor assembly of between about 0.01 to about 10,000 micro-strain.

2. The apparatus of claim 1, wherein the portion of the passive electrical resonant circuit of the at least one sensor assembly is operably coupled to an exterior surface of the implant.

3. The apparatus of claim 2, wherein the portion of the passive electrical resonant circuit of the at least one sensor assembly is integrally coupled to an exterior surface of the implant.

4. The apparatus of claim 1, wherein the passive electrical resonant circuit of each at least one sensor is encapsulated in a housing.

5. The apparatus of claim 1, wherein the passive electrical resonant circuit of the at least one sensor assembly comprises a LC resonant circuit.

6. The apparatus of claim 5, wherein the LC resonant circuit of the at least one sensor assembly comprises a coil inductor operably coupled to a capacitor.

7. The apparatus of claim 6, wherein the inductance of the LC resonant circuit is between about 5 to about 15 micro-Henry.

8. The apparatus of claim 6, wherein the resonant frequency of the LC resonant circuit is between about 25 to about 45 MHz.

9. The apparatus of claim 6, wherein the capacitance of the LC resonant circuit is between about 1 to about 20 pF.

10. The apparatus of claim 6, wherein the coil inductor is a substantially planar spiral inductor.

11. The apparatus of claim 6, wherein the coil inductor has a longitudinal axis and wherein the coil inducted is elongated about the longitudinal axis.

12. The apparatus of claim 1, wherein the implant comprises an elongated rod operably coupled to a plurality of vertebra, and wherein the portion of the passive electrical resonant circuit of the at least one sensor assembly is operably coupled to an exterior surface of the rod.

13. The apparatus of claim 12, wherein the at least one sensor assembly comprises a plurality of sensor assemblies.

14. The apparatus of claim 13, wherein the plurality of sensor assemblies are positioned substantially co-planer.

15. The apparatus of claim 13, wherein the plurality of sensor assemblies are positioned substantially in a plane that is substantially transverse to a longitudinal axis of the implant.

16. The apparatus of claim 12, wherein the passive electrical resonant circuit of the at least one sensor assembly comprises a LC resonant circuit comprising a coil inductor operably coupled to a capacitor; and wherein the passive electrical resonant circuit of the at least one sensor assembly is coupled thereto the exterior surface of the rod such that the capacitor is positioned substantially in a plane that is substantially transverse to a longitudinal axis of the implant.

17. The apparatus of claim 1, wherein the implant comprises an elongated rod operably coupled to a plurality of vertebra, further comprising a sleeve member configured to mount thereon a select portion of the elongated rod, wherein the at least one sensor assembly is coupled to an interior surface of the sleeve member.

18. The apparatus of claim 17, wherein the portion of the passive electrical resonant circuit of the at least one sensor assembly is positioned in contact with the exterior surface of the rod when the sleeve member is mounted to the select portion of the elongated rod.

19. The apparatus of claim 18, wherein the at least one sensor assembly comprises a plurality of sensor assemblies.

20. The apparatus of claim 19, wherein the plurality of sensor assemblies are positioned substantially co-planer.

21. The apparatus of claim 19, wherein the plurality of sensor assemblies are positioned substantially in a plane that is substantially transverse to a longitudinal axis of the implant.

22. The apparatus of claim 1, wherein the passive electrical resonant circuit of the at least one sensor assembly comprises a conductive wire coil circuit.

23. The apparatus of claim 20, wherein the implant is an elongated polymeric rod operably coupled to a plurality of vertebra, and wherein the conductive wire coil circuit is connected to and is wrapped about a portion of the exterior surface of the polymeric rod.

24. The apparatus of claim 23, wherein the inductance of the conductive wire coil circuit is between about 5 to about 15 micro-Henry.

25. The apparatus of claim 23, wherein the resonant frequency of the conductive wire coil circuit is between about 25 to about 45 MHz.

26. The apparatus of claim 23, wherein the capacitance of the conductive wire coil circuit is between about 1 to about 20 pF.

27. A system for sensing strain on a portion of an implant positioned in a living being, the system comprising:
   an ex-vivo source of RF energy;
   at least one sensor assembly mountable thereto a portion of the implant and comprising a passive electrical resonant circuit, wherein the passive electrical resonant circuit is configured to be selectively electromagnetically coupled to the ex-vivo source of RF energy, and wherein, in response to the electromagnetic coupling, each sensor assembly is configured to generate an output signal characterized by a frequency that is dependent upon urged movement of a portion of the passive electrical resonant circuit between about $10^{-12}$ m to about $10^{-4}$ m; and
   a receiver configured for receiving the output signal, wherein the characterized frequency is indicative of strain applied thereon the portion of the of the passive electrical resonant circuit of the respective sensor assembly, and wherein the receiver comprises a non-implantable remotely operated receiver.

28. The system of claim 27, further comprising means for calibrating the at least one sensor assembly.

29. The system of claim 27, wherein the passive electrical resonant circuit of each at least one sensor is encapsulated in a housing.

30. The system of Claim 27, wherein the passive electrical resonant circuit of the at least one sensor assembly comprises a LC resonant circuit.

31. The system of claim 30, wherein the LC resonant circuit of the at least one sensor assembly comprises a coil inductor operably coupled to a capacitor.

32. The system of claim 30, wherein the inductance of the LC resonant circuit is between about 5 to about 15 micro-Henry.

33. The system of claim 30, wherein the resonant frequency of the LC resonant circuit is between about 25 to about 45 MHz.

34. The system of claim 30, wherein the capacitance of the LC resonant circuit is between about 1 to about 20 pF.

35. The system of claim 27, wherein the passive electrical resonant circuit of the at least one sensor assembly comprises a conductive wire coil circuit.

36. The system of claim 35, wherein the implant comprises an elongated polymeric rod operably coupled to a plurality of vertebra, and wherein the conductive wire coil circuit is connected to and is wrapped about a portion of the exterior surface of the polymeric rod.

37. The system of claim 35, wherein the inductance of the conductive wire coil circuit is between about 5 to about 15 micro-Henry.

38. The system of claim 35, wherein the resonant frequency of the conductive wire coil circuit is between about 25 to about 45 MHz.

39. The system of claim 35, wherein the capacitance of the conductive wire coil circuit is between about 1 to about 20 pF.

40. The apparatus of claim 27, wherein the implant comprises an elongated rod operably coupled to a plurality of vertebra, and wherein the at least one sensor assembly is coupled to an exterior surface of the rod.

41. The system of claim 27, further comprising a means for monitoring the output signal of the at least one sensor assembly.

42. The system of claim 41, wherein the means for monitoring the output signal of the at least one sensor assembly comprises a processor configured to determine the relative strain applied to the at least one sensor assembly based on the frequency of the output signal.

43. The system of claim 27, wherein the portion of the passive electrical resonant circuit of the at least one sensor assembly is operably coupled to an exterior surface of the implant.

44. The system of claim 43, wherein the portion of the passive electrical resonant circuit of the at least one sensor assembly is integrally coupled to an exterior surface of the implant.

* * * * *